(12) United States Patent
Haselton et al.

(10) Patent No.: US 7,521,261 B2
(45) Date of Patent: Apr. 21, 2009

(54) METHOD FOR SCREENING MOLECULAR INTERACTIONS

(75) Inventors: Rick Haselton, Nashville, TN (US); Mark McQuain, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/529,197

(22) PCT Filed: Sep. 26, 2003

(86) PCT No.: PCT/US03/30623

§ 371 (c)(1), (2), (4) Date: Jan. 30, 2006

(87) PCT Pub. No.: WO2004/029217

PCT Pub. Date: Apr. 8, 2004

(65) Prior Publication Data

US 2006/0121481 A1 Jun. 8, 2006

Related U.S. Application Data

(60) Provisional application No. 60/413,828, filed on Sep. 26, 2002.

(51) Int. Cl.
*G01N 33/543* (2006.01)

(52) U.S. Cl. .................................... 436/518

(58) Field of Classification Search ................ 436/518, 436/514, 4, 7.1; 435/4, 7.1
See application file for complete search history.

(56) References Cited

U.S. PATENT DOCUMENTS

| | | | |
|---|---|---|---|
| 3,818,444 A * | 6/1974 | Connell | 235/462.39 |
| 4,223,002 A * | 9/1980 | Newman | 436/542 |
| 4,824,776 A | 4/1989 | Heller | 435/6 |
| 5,001,051 A | 3/1991 | Miller et al. | 435/6 |
| 5,364,797 A | 11/1994 | Olson et al. | 436/501 |
| 5,445,935 A | 8/1995 | Royer | 435/6 |
| 5,843,767 A | 12/1998 | Beattie | 435/287.1 |
| 6,287,765 B1 | 9/2001 | Cubicciotti | 435/6 |
| 6,288,220 B1 | 9/2001 | Kambara et al. | 536/24.31 |
| 7,015,047 B2 * | 3/2006 | Huang et al. | 436/526 |
| 2002/0006643 A1 * | 1/2002 | Kayyem et al. | 435/91.2 |

OTHER PUBLICATIONS

Fredrickson et al., "Towards environmental toxicogenomics—development of a flow-through, high-density DNA hybridizationarray and its application to ecotoxicity assessment", *Sci Total Environ*, 274:137-149, 2001.

Luo and Geschwind, "Microarray applications in neuroscience", *Neurobiol Dis*, 8:183-193, 2001.

* cited by examiner

*Primary Examiner*—Ann Y Lam
(74) *Attorney, Agent, or Firm*—Fulbright & Jaworski, LLP

(57) ABSTRACT

Systems and methods are described for screening molecular interactions using a filamentous based platform for molecule presentation. Method includes screening for protein-protein, DNA-DNA and other chemical interactions.

75 Claims, 11 Drawing Sheets

1 2 3 4

METHOD FOR SCREENING MOLECULAR INTERACTIONS

The present invention claims benefit of priority to U.S. Provisional Ser. No. 60/413,828, filed on Sep. 26, 2002, the entire contents of which are hereby incorporated by reference.

This invention was made with government support under grant number 5R21EB003516 awarded by the National Institutes of Health. The government has certain rights in the invention.

BACKGROUND OF THE INVENTION

1. Field of the Invention

The invention relates generally to the field of molecular screening. More particularly, the invention relates to biomolecular assays. Specifically, specific embodiment of the invention relates to the screening of DNA-DNA interactions, DNA-protein interactions, or protein-protein interactions, using probes disposed on a filamentous substrate.

2. Discussion of the Related Art

Assays based on interactions between living cells and substances, biomolecules or cellular structures offer enormous possibilities for screening and semi-quantitative analysis. The principles of the assays can range from relatively simple ligand-receptor interactions, to cell-based assays using genetically modified cells.

Biomolecular screening technologies are currently characterized by the attachment of unique molecular structures at known physical locations on a surface. Unknown molecular partners from a fluid phase are captured at specific locations in the two-dimensional surface, and some of the characteristics of these unknown structures are determined. Such method can be characterized as Eulerian in nature, since known "probes" are fixed in space.

Problems with current technologies include low sensitivity, slow and non-uniform delivery of liquid-phase binding partners, large sample volume requirements which often necessitate pre-hybridization amplification techniques. Another problem with current microarray technology includes difficulty of automation, which may include multiple fluid handling steps during slide processing, raster scanning, and image analysis.

Heretofore, the requirements of a biomolecular screening method and/or apparatus which provides high sensitivity, fast and uniform delivery of liquid-phase binding partners, and demands small sample volumes, have not been fully met. Thus, what is needed is a solution that addresses all of these requirements.

SUMMARY OF THE INVENTION

The present invention provides a novel biomolecular screening technology based on a Lagrangian method that is a solution to the above mentioned problems and also creates new areas of application. According to the present invention, various probes are utilized in conjunction with a filamentous support, and their interaction with unknown fluid-phase structures is assessed by transporting the filament through one or more chambers containing the unknown structures.

In one embodiment, there is provided a method of detecting target-probe interactions comprising (a) providing a filament with a first probe disposed thereon; (b) traversing the filament through a first chamber, wherein the first chamber contains the target in solution; and (c) assessing binding of the target to the first probe. The first probe may be disposed on the filament in an annular fashion. The first probe also may be associated with a probe identifier. The filament may have a plurality of different probes disposed thereon, and the plurality of different probes may be disposed in a single ring around the filament. Each of the plurality of different probes may be associated with a distinct probe identifier.

The method may further comprise traversing the filament through a second chamber, wherein the second chamber contains a solution that lacks the target. The second chamber may comprise a solution for pre-processing or post-processing of the filament. Preprocessing may comprise making an array, chemical blocking of a reactive group on the target, ionic blocking of a target, or denaturing of a target, while post-processing may comprise deblocking of a reactive group on the target, removal of an ionic blocker, or renaturing of a target molecule.

The target may be labeled with a fluorescent label, a chemilluminescent label, a radioactive label, a magnetic label, or a spin resonance label. The probe identifier may be a bar code, for example, disposed in an annular fashion around the filament, or in a linear fashion. The method may further comprise convective transport of the target solution by means of filament movement through the first chamber. The filament may comprise surface features to enhance mixing of the target solution, such as those that enhance mixing of the target solution. The filament also may be adapted to incorporate an electrical charge, and used to subject the target to electrophoretic movement. The electrophoretic movement may promote or inhibit target-probe interaction.

The method may further comprise a second traversing of the filament through a chamber comprising the target. The chamber used for the second traversing may be the same chamber as used for the initial traversing with the target, or it may be different. The temperature, charge, amperage, voltage or polarity in the chamber used for the second traversing may be different from that use for the initial traversing. The charge in the chamber used for the second traversing may also be altered from that used in the initial traversing. The method may further comprise re-circulating target solution from the first chamber.

The method may further comprise enhancing detection of binding of the target to the first immobilized probe. The enhancing may comprise traversing the filament through a second processing chamber that contains (i) a second liquid phase probe that binds to the target at a location distinct from the first immobilized probe, and wherein the second liquid phase probe contains a binding site for a third liquid phase probe; and (ii) a third liquid phase probe that is detectable. The third liquid phase probe may be provided in an inactive state and then activated to facilitate amplification. The third liquid phase probe may be labeled with a fluorescent, a chemilluminescent or a radioactive molecule. The third liquid phase probe may be a linear molecule with a binding site for itself, or even a branched molecule with multiple binding sites for itself.

The filament may be about 1 µm to about 0.5 cm in diameter. The processing chamber may be greater than 1 µm in diameter and less than 2.0 cm. The target solution in the processing chamber may be present in a volume of less than 100 µl. The fiber may comprise an axial or radial probe density of greater 1 probe region per cm. The filament may be transparent.

In another embodiment, there is provided an apparatus comprising one or more chambers, each chamber comprising two surface tension valves permitting a filament to move into and out of the chamber. More specifically, the apparatus may comprise a processing chamber and a wash chamber, a first processing chamber and a second processing chamber, or a processing chamber and an amplification chamber. The apparatus may further comprise a signal detection device, such as one that comprises an optical sensor. The apparatus may further comprise a signal generating device, such as one that comprises an electromagnetic radiation source, such as a laser. The chambers of the apparatus may further comprise a sealable port, distinct from the surface tension valve, for the insertion or withdrawal of a solution.

In yet another embodiment, there is provided a filament having a substantially cylindrical shape with a first set of identical probes disposed on the filament in an annular fashion. The filament may further comprise a second set of identical probes disposed on the filament in an annular fashion. The filament may also further comprising a third, fourth, fifth, sixth, seventh, eighth, ninth and/or tenth set of identical probes disposed on the filament in an annular fashion. The filament may further comprising a probe identifier associated with each set of probes, such as a bar code. The probe may be a nucleic acid or mimetic, for example, a DNA or an RNA. The probe also may be a peptide or protein or mimetic. The filament may be transparent. The filament also may comprise one or more surface features selected from the group consisting of pores, abrasions, invaginations or protrusions.

In still yet another embodiment, there is provided a system for assessing target-probe interactions comprising (a) a first processing chamber comprising first and second surface tension valves permitting a filament to move into and out of the chamber; (b) a filament disposed in the first processing chamber, passing through the first and second surface tension valves; said filament having probes disposed thereon in an annular fashion; and (c) a device for identifying target-probe interactions on the filament. The system may further comprise a washing chamber comprising first and second surface tension valves permitting a filament to move into and out of the chamber. The system also may further comprise a second processing chamber comprising first and second surface tension valves permitting a filament to move into and out of the chamber.

The device for identifying target-probe interactions may be an excitation source coupled to an emission sensor, for example, where the excitation source is an electromagnetic, chemical, enzymatic excitation or light source. The light source may be a laser. The filament may further comprise a probe identifier associated with a particular probe type. The system also may further comprise one or more pumps operably connected to the processing chamber by a tube and/or valve, facilitating filling or draining of the processing chamber with a solution; may further comprise a device that facilitates transport of the filament through the first processing chamber; may further comprise a device for applying a first electrical charge to the filament; may further comprise a second device for applying a second electrical charge to the filament, the second electrical charge being opposite that of the first electrical charge; and may further comprise a device for subjecting a target in solution in the processing chamber to electrophoretic transport.

The filament may be looped to facilitate repeated exposure to the first processing chamber, the target and probe may be nucleic acids, or they may be proteins. The system any further comprise a computer that controls one or more of (i) filament movement; (ii) filling or draining of the processing chamber; (iii) temperature of a solution in the processing chamber; (iv) charge on the filament; (v) electrophoretic transport of the target; (vi) analysis of a signal resulting from target-probe binding; and (vii) signal amplification.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly. The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term deploying, as used herein, is defined as designing, building, shipping, installing and/or operating. The term means, as used herein, is defined as hardware, firmware and/or software for achieving a result. The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system. The phrase any integer derivable therein, as used herein, is defined as an integer between the corresponding numbers recited in the specification, and the phrase any range derivable therein is defined as any range within such corresponding numbers.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

DESCRIPTION OF PREFERRED EMBODIMENTS

Figure 1:
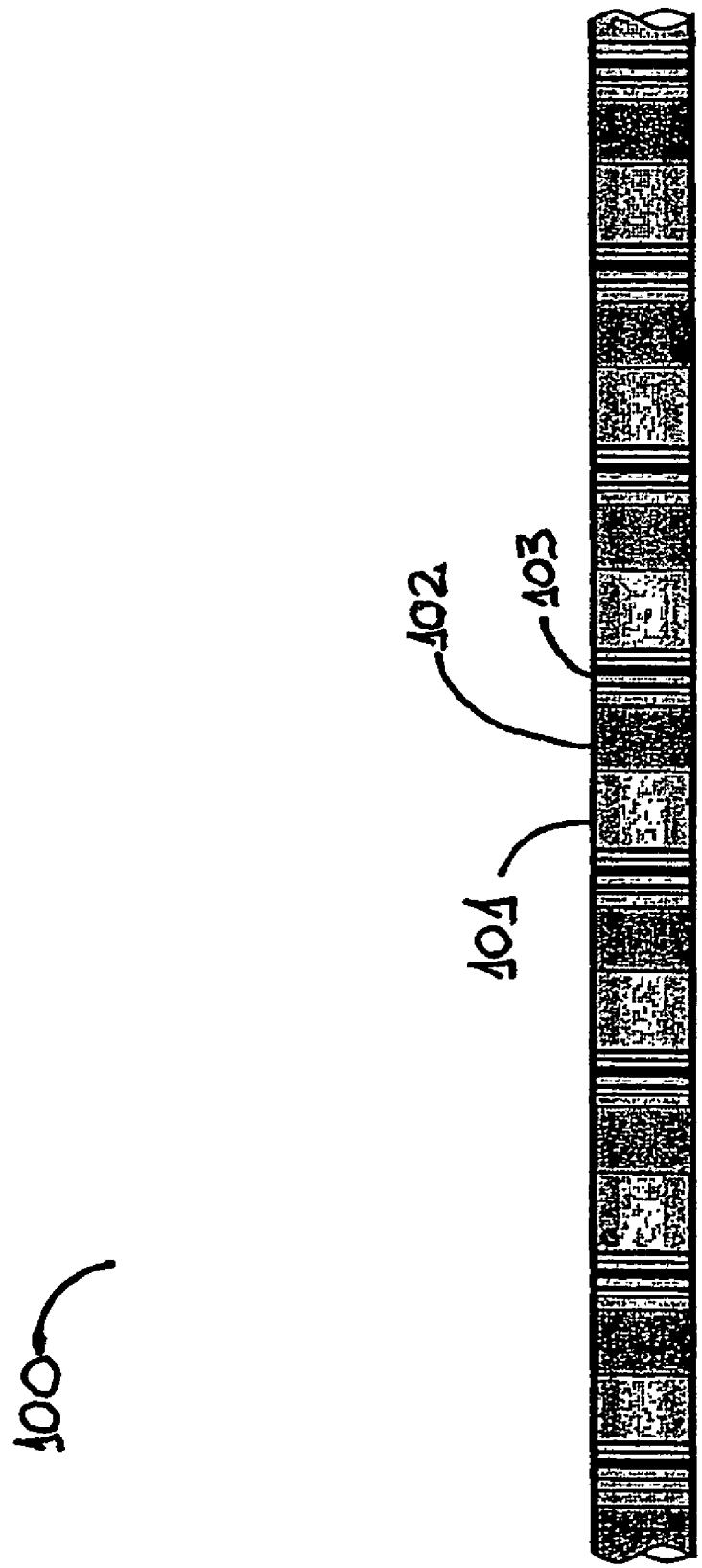
FIG. 1 illustrates a diagram of a linear filament, representing an embodiment of the invention.

Assessing interaction of biomolecules is a major aspect of biotech research. Many important drugs and drug targets have been identified using just such assays. In general, the screening of DNA-DNA interactions, DNA-protein interactions, and protein-protein define a wide variety of assays regularly conducted by researchers. Other interactions, such as agonist-receptor interactions, antibody-antigen interactions, and drug-drug target interactions provide additional examples.

Current biomolecular screening technologies are characterized by attachment of unique molecular structures at known physical locations on a two-dimensional surface, capture of unknown molecular partners from a fluid phase at specific locations in the two-dimensional structure, and determination of the coordinates and hence the characteristics of the unknown structures captured from the fluid phase.

The present invention provides a novel approach to biomolecular screening technology, wherein probes are rendered "mobile" by disposing them on a filamentous substrate which can be easily manipulated through various "zones" of an apparatus or system. The different zones provide contact with various solution, including those which contain unknown structures. The identity of the probes may be preserved by their association with an adjacent identifier. Thus, the present invention can solve many problems currently limiting the application of biomolecular screening technologies and create new areas of application as well.

A. The Probe Filament

In the most fundamental sense, the present invention relies upon the use of a filamentous probe support as a platform for assessing biomolecular interactions. The advantages provided by the filamentous support are numerous, but in particular, it provides the opportunity to rapidly and efficiently move probes between different zones of an apparatus and still retain information about their location. It also permits the use of very small volumes of various samples—as little as nanoliter volume reactions. The linear probe filament may be constructed so that the probes are arranged in an annular fashion, forming a probe band around the circumference of the filament. This also permits bands to be deposited so as to achieve high linear density of probes on the filament.

The filament may be made of any of a number of different materials. Suitable materials include polystyrene, glass (e.g., fiber optic cores), nylon or other substrate derivatized with chemical moieties to impart desired surface structure (3-dimensional) and chemical activity. The filament may also be constructed to contain surface features such as pores, abrasions, invaginations, protrusions, or any other physical or chemical structures that increase effective surface area. These surface features may, in one aspect, provide for enhanced mixing of solutions as the filament passes through a solution-containing chamber, or increase the number and availability of probe molecules. The filament may also contain a probe identifier which allows the user to track large numbers of different probes on a single filament. The probe identifiers may be dyes, magnetic, radioactive, fluorescent, or chemilluminescent molecules. Alternatively, they may comprise various digital or analog tags.

In a particular embodiment, the filament can also be adapted to incorporate charge and current. This can facilitate electrophoretic movement of target molecules toward the probe to enhance interactions. Conversely, the charge/current may be used to drive off unwanted target that is non-specifically bound to the probe filament. For example, a conductive filament could be attached to positive voltage to attract negatively charged nucleic acids or proteins, facilitating and increasing target-probe interactions. Following this interaction, a negative voltage could be applied to the filament to repel non-specifically attached targets. The strength of the voltage could be modulated to achieve the desired stringency of probe-target interactions.

Referring to FIG. 1, a diagram of a linear filament is depicted. A probe 102 is coupled to a substrate filament 101. A probe identifier 103 is placed adjacent to the probe 102. In a preferred embodiment, a plurality of probes is coupled to the substrate filament 101, and each probe is coupled to its own probe identifier. In another embodiment, an array of probes is coupled to a single probe array identifier, wherein the single probe array identifier contains information regarding each probe of the array.

Still referring to FIG. 1, it can be advantageous to design the linear filament with small dimensions. For example, the diameter of the probe can be of the order of 1 μm to 0.5 cm, for example, 30 μm as illustrated. Probe regions may be separated by distances on the order of 1 cm or less. The small dimensions provide numerous advantages, including high sensitivity, fast and uniform delivery of liquid-phase binding partners, and small reaction volume requirements.

B. Probes and Targets

Another important aspect of the invention is the probes which are disposed on the surface of the filament; and the targets to which these probes bind. As discussed above, the probes can be any of a wide variety of biomolecules including nucleic acids (DNAs, RNAs), proteins, amino acids, small organic molecules, etc. For two nucleic acids, the binding interaction will generally be characterized by hybridization, achieved by homologous base pairing. For one or more protein molecules, the interaction will generally be the formation of protein-ligand complexes which are reliant on the complementary structure and charge of the component molecules. Various types of molecules suitable for use in accordance with the present invention are described below.

1. Nucleic Acids

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double stranded nucleic acid by the prefix "ds," and a triple stranded nucleic acid by the prefix "ts."

(a) Nucleobases, Nucleosides, Nucleotides and Analogs Thereof

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions with respect to hybridization behavior. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference). Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as flourescent nucleic acids probes; U.S. Patent 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Patent 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes olignucleotides conjugated to anthraquinone at the 5' terminus that possess enhanced hybridization to DNA or RNA; enhanced stability to nucleases; U.S. Pat. No. 5,700,922 which describes PNA- DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

(b) DNA

DNAs are defined as nucleic acids containing adenine "A," guanine "G," thymine "T" and cytosine "C." DNA molecules, both single- and double-stranded, may be utilized in accordance with the present invention. DNAs may comprise coding sequences or non-coding sequence, and genomic sequences or cDNAs, synthesized strands homologous to the target of interest. DNA "arrays"—collections of DNAs that represent a group of selected probes.

(c) RNA

RNAs are defined as nucleic acids containing A, G, uracil "U" or C. Both single- and double-stranded RNAs, may be utilized in accordance with the present invention. Because of their labile nature, additional steps must be take to preserve the integrity of RNA containing samples. In particular, the ubiquitous presence of RNAses requires the use of RNAse inhibitors such as DEPC.

2. Proteins

In another embodiment, the probe may be a proteinaceous compound. There are wide variety of protein-protein interactions; however, proteins also bind nucleic acids, metals and other non-proteinaceous compounds (e.g., lipids, hormones, transmitters). Some examples of protein that may be used as either targets or probes are listed below.

(a) Antibodies

Antibodies may be used as probes for unknown molecules, or they maybe the target for reaction with a known probe. The antibodies may be either polyclonal or monoclonal in origin. Method for preparing antibodies are well known to those of skill in the art and need not be discussed here. Antibodies may be fixed to the filament support using standard techniques.

Obviously, identifying antibodies that bind to certain target molecules is an important goal that could be accomplished by the present invention. However, the present invention also permits the screening of samples for the presence of antibodies. For example, a filament might contain a variety of bacterial and viral antigens, which could assist in diagnosis of infectious disease by identifying relevant antibodies in an affected subject.

(b) Enzymes

Enzymes are proteins that facilitate the modification of a wide variety of compounds including nucleic acids, other proteins, lipids, sugars, steroids and many other compounds. Particular types of assays contemplated include identifying inhibitors of enzymes that bind to, but are not processed by, the enzyme. Alternatively, identifying compounds that are bound by an enzyme may assist in design of pro-drugs that are processed by an enzyme.

(c) Receptors

Receptors are molecules that facilitate signaling processes by binding their cognate ligand moieties. Once bound, the receptor will then perform some other function (enzymatic, intracellular translocation, cell permeability) that effects the signaling. Identifying molecules that block receptor function, or mimic the natural ligand, can be accomplished using the present invention.

(d) DNA-binding Proteins

Another important class of proteins is the DNA binding proteins. These proteins include polymerases, helicases, ligases, and transcription factors. The proteins have varying degrees of DNA sequence specificity can be assessed for ability to bind varying DNA sequences. Conversely, providing a DNA sequence as a probe, once can identify unknown binding proteins with specificity for that sequence.

3. Small Molecules Libraries

A wide variety of "small molecules" can be examined for their ability to bind to a given probe. These libraries, comprises of non-protein, non-nucleic acid molecules are commercially available from a variety of sources. Alternatively, libraries can be constructed around particular "pharmacores" that are believed to provide basic structural features necessary for a particular drug to function.

4. Labels

In various embodiments, it may desirable to label probe or target molecules. Examples of labels include paramagnetic ions, radioactive isotopes; fluorochromes, NMR-detectable substances, and X-ray imaging compounds.

Paramagnetic ions include chromium (III), manganese (II), iron (III), iron (II), cobalt (II), nickel (II), copper (II), neodymium (II), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection.

Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850, 752; 3,939,350; 3,996,345; 4,277,437; 4,275,149 and 4,366, 241; each incorporated herein by reference.

C. The Processing Chambers

In order to take advantage of the linear filamentous support, the present inventors have designed processing chambers, equipped with liquid-miscible valves, that permit the passage of through the filament into and out of the chamber without substantial loss of fluids, and preservation of each compartment's integrity. In a preferred embodiment, the processing chambers are configured to provide down to nanoliter volumes. Processing, hybridization, and analysis steps can be conducted in a series of separate chambers, or in contiguous compartments within a single chamber.

Figure 2:
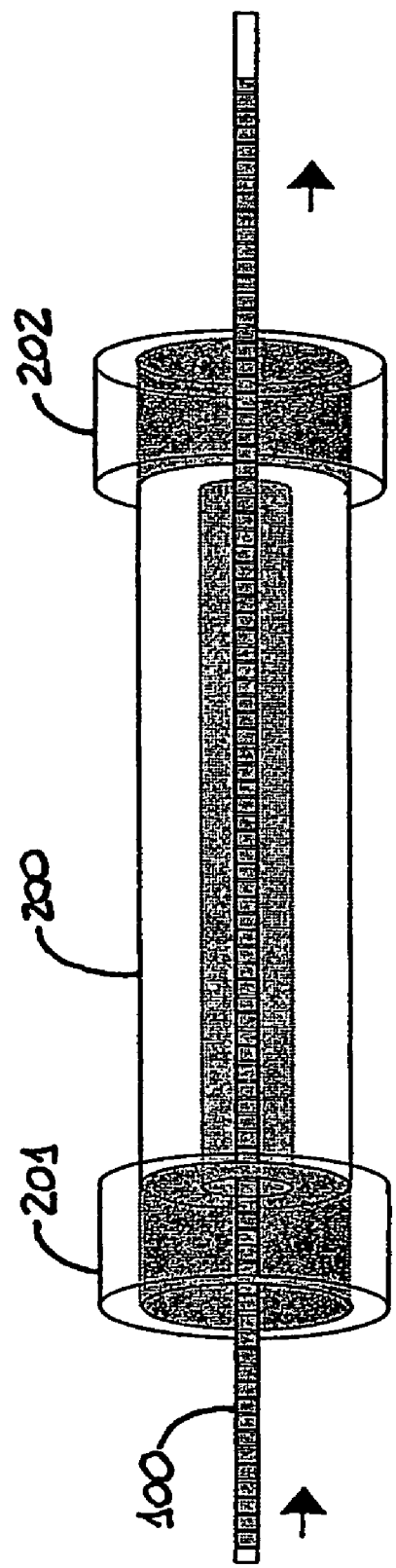
FIG. 2 illustrates a diagram of a processing chamber, representing an embodiment of the invention.

Referring to FIG. 2, a diagram of a processing chamber 200 is depicted. A processing solution is contained in the tube 200. A first valve 201 and a second valve 202 seal the ends of the chamber. The filament 100 enters the chamber 200 via the first valve 201, and exits via the second valve 202. Still referring to FIG. 2, the pair of valves 201-202 can be surface tension valves. Surface tension valve fluids should be immiscible with the processing solution contained in the tube 200, preferentially occupy the larger diameter valve portion of the chamber and not displace the reagent liquid in the process chamber. Other characteristics may include low vapor pressure and low surface tension.

Figure 3:
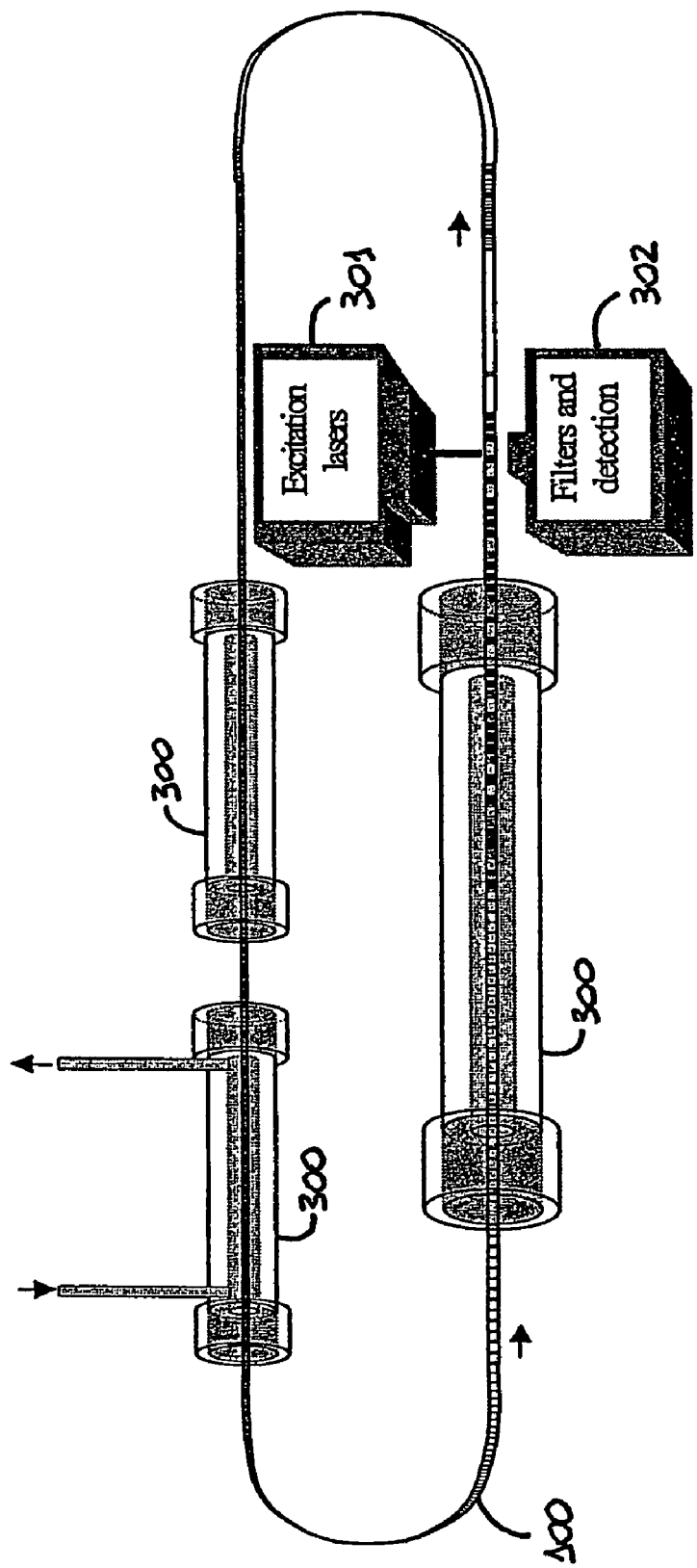
FIG. 3 illustrates a diagram of a system, representing an embodiment of the invention.

The chamber may further comprise connections and/or openings for introduction or flow through of fluids (as illustrated the chambers designated 301 in FIG. 3).

Still referring to FIG. 2, it is advantageous to design the chamber 200 to small dimensions. For example, a 2 cm section of a 30 μm diameter linear filament surrounded by a tube 201 with a 50 μm inner diameter requires only 60 nl to fill, which is 2 to 3 orders of magnitude less than typical volumes used in current microarray techniques. Use of such small volumes, in addition to reducing costs, also permits more facile achievement of high target DNA concentrations, which are sometimes required for effective binding of target to probe.

1. Processing Chambers

A variety of different types of chambers may be used in accordance with the present invention. Clearly, a processing chamber containing putative target molecules for binding is an important feature of the invention. It also is possible, where convenient, to have a series of processing chambers that are connected by means other than the filament. For example, one may wish to "recycle" target solution by moving it from one chamber to another for reuse. A processing chamber may also be reused in the sense that the filament may be passed through a given the chamber more than once.

The present invention may utilize multiple processing such chambers where different target solutions included therein. Thus, a single filament can be utilized for multiple reactions in a single "run." If a large number of reactions are to be run, a series of processing chambers may be utilized that can quickly be emptied, rinsed, and filled with new target solutions. Thus, one can image an apparatus with three processing chambers A, B and C, where after a filament passes through each chamber (A→B→C), the chambers can be emptied and refilled with new target solutions, and the movement of the filament is reversed (C→B→A). By repeating this process two more times, a series of four filament passes permit exposure to twelve different target solutions.

2. Pretreatment Chambers

It is often the case that probes or filaments will be "pretreated" in such a way as to ensure that the ensuing reaction with the target has a high degree of fidelity, i.e., minimize non-specific attachment. A classic example is of a pretreatment is a "blocking" reaction. Non-specific protein-protein interactions by inhibited by pretreating a substrate with a non-specific protein such as BSA. Similarly, non-specific DNA reactions can be reduced by incubating the probe with a "random" DNA known to lack homology with the probe.

3. Wash Chambers

Another important step when assessing the reaction of biomolecules is to remove non-specifically bound molecules from the probe. Though achieving the same goal as pretreatment, washing takes place after the exposure of probe to target. Typically, a wash solutions comprise a buffer similar to that used in the target solution, but lacking the target itself. Occasionally, it will be desirable to alter the chemical properties of the wash solution by, for example, changing the salt concentration or pH.

4. Amplification Chambers

As will be discussed in greater detail below, it may be desirable to recursively amplify signals relating to binding of targets to probe. There are a variety of mechanisms for accomplishing this. However, a common feature will be the need for one or more chambers which effect the necessary steps to achieve the amplification.

D. The System

One of the most striking characteristics of the invention is the extraordinary reduction in dimensions and volumes of the molecular screening system. The reduction in scale is augmented by the geometry of the concentric cylindrical design of the filament and chambers, which increases surface to volume ratios. Further, enhanced molecular interactions can be achieved by convective transport of liquid resulting from the movement of the probe filament through the processing chambers. Small and convectively mixed volumes can provide efficient and accurate interactions. Further, the rate of target-probe interaction can be increased by decreasing volumes, thereby decreasing the target to probe distance and increase target concentrations.

Referring to FIG. 3, a diagram of a system is depicted. A filament 100 circulates through a set of chambers 300. Each of the chambers can represent an individual pre-processing, processing, or post-processing steps. In a particular embodiment, an excitation laser 301 is positioned to interrogate the filament 100, and a detector 302 is positioned to measure emissions from the filaments.

Another advantage of the system is the facilitation of directed path or knowledge guided analysis. Results from hybridization of initial probes, combined with knowledge based on gene defect probabilities, can be used to direct filament movement to test hybridization of specific probes of interest at specific regions on the filament. Similarly, for DNA-protein interactions, binding might indicate that a second related filament location be tested next.

Still referring to FIG. 3, the filament will be moved through the different processing chambers by a mechanical transport mechanism. This can be accomplished by using paired wheels, separated by the diameter of the filament, which rotate in opposite directions and pull the filament through various chambers. This transport mechanism can be linked to a control unit (e.g., a computer), which can reverse the direction of transport to repeat any necessary step. The control unit may also provide variable speeds for different "zones" within the system, including causing the filament to become stationary at some points.

Another aspect of the system which is not illustrated in FIG. 3 is the potential to provide a system for filling and emptying the various chambers with appropriate solutions. This can be done by attaching fill and drain tubes to the chambers via openings which include water-tight valves. Alternatively, the openings may be fixed and the tubes may provide for constant transport of appropriate solutions through the chambers.

Various other aspects of the system are described below.

1. Electrophoretic Target Transport

Electrophoretic target transport is another mechanism of transport that is conducive to the linear filament design. Maintenance of an electrical gradient to drive the processing solution to the filament surface can be utilized to speed binding reactions. Standard methods are available to control the electrical potential of the fiber with respect to the surrounding solution.

Figure 10:
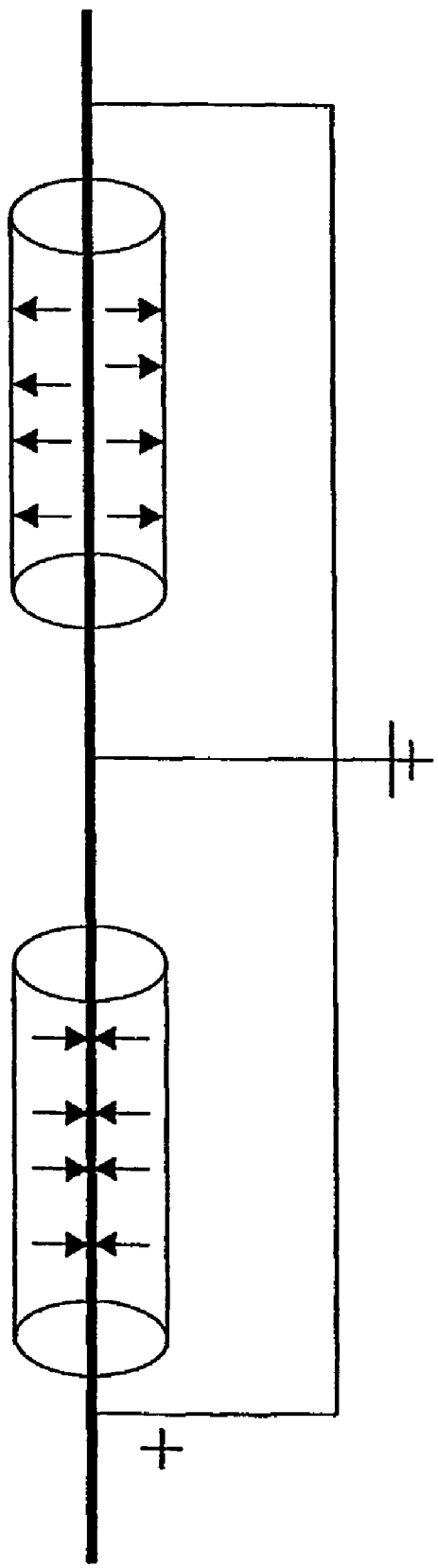
FIG. 10 shows an example of electrophoretic transport.

By way of example, applicants provide FIG. 10. DNA target in solution is negatively charged. Applying current to the filament in a first chamber creates a positively charged electrode, which attracts the negatively charged DNA, thereby facilitating interactions with the filament-bound probe. Moving into a second chamber, the current is reversed, causing the filament to be negatively charged, which will repel any non-specifically bound target DNA Wolfe et al, 2000).

2. Post-Hybridization Amplification

In another embodiment, the system may include mechanisms for amplifying reaction signals. Specifically, the inventors contemplate the use of recursive signal amplification to enhance the detectability of the hybridized target. One strategy uses dendrimers or molecules with multiple binding sites—a binding site for a fixed molecule and at least one binding site for a subsequent indicator molecule. In advantageous embodiments, the dendrimers contain blocked binding sites to avoid binding to each other.

Figure 4:
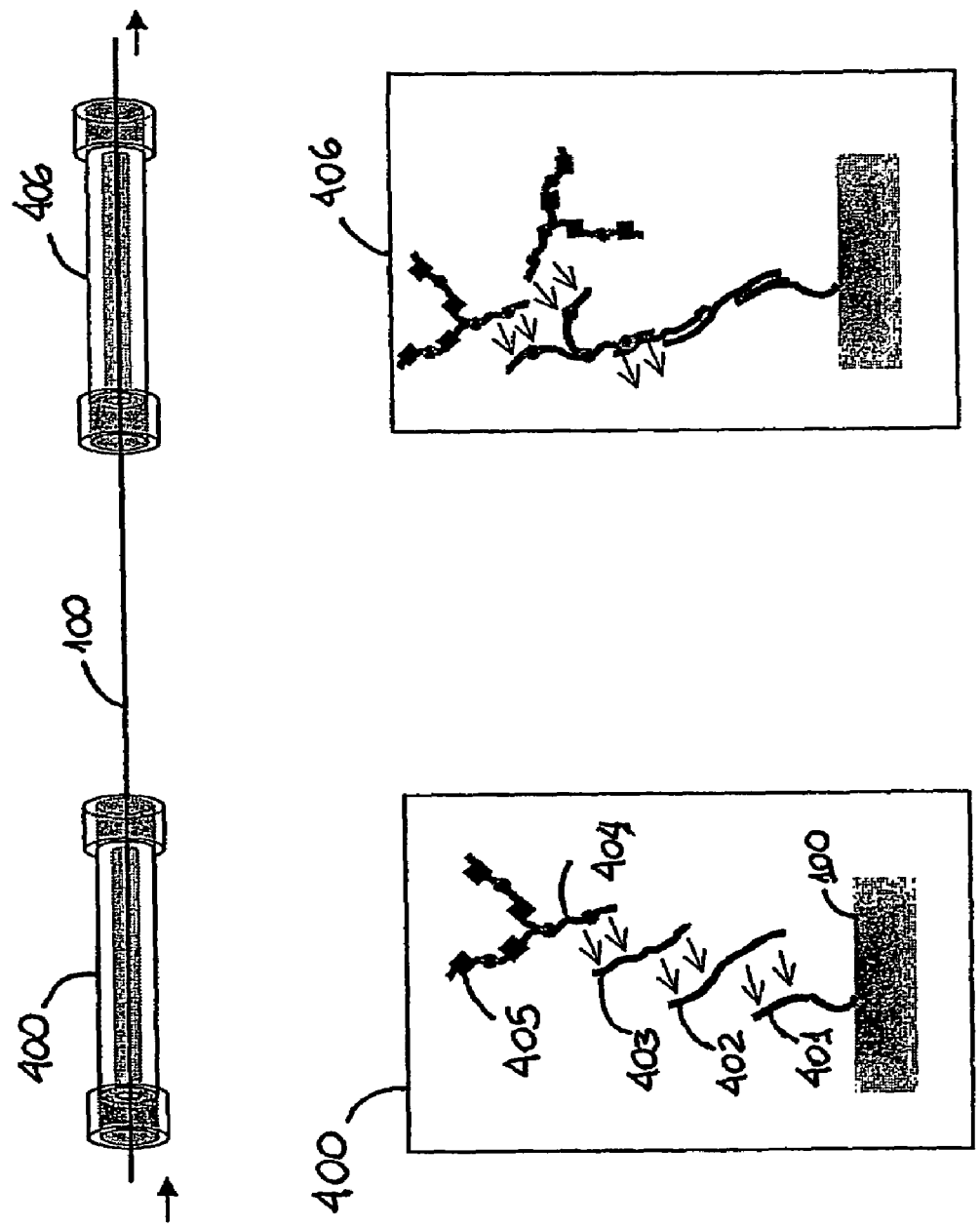
FIG. 4 illustrates a diagram of a recursive post-hybridization amplification strategy, representing an embodiment of the invention.

Referring to FIG. 4, a diagram of a post-hybridization DNA strategy is depicted. In an initial round of target-probe specific hybridization 400, an anchored probe 401 binds to a solution phase hybridization complement 402. The binding of these partners can be detected by the presence of a fluorescent label incorporated within the solution phase hybridization complement 402. The filament can then be processed and scanned with a standard flat-bed scanner to measure the level of fluorescence at each probe location, or the filament can be repositioned to read fluorescence at this location using the apparatus described herein.

Still referring to FIG. 4, the invention can also include the addition of two DNA structures to take advantage of the feedback potential of the detection methodology. A first component 403 can be a unique DNA structure with a region complementary to the solution phase target molecule 402 and a region complementary to a single tail region of a second component 404. Each first component 403 structure is designed to achieve hybridization with a particular solution phase target. The second component 404 contains a 3' end sequence which is complementary to the 5' end sequence of the second component 404 and incorporates a fluorescent label 405. One skilled in the art will realize more than one fluorescent label may be utilized.

Still referring to FIG. 4, the 5' end sequence of the second component 404 is preferably inactivated and incapable of forming loop structures in solution. Recursive amplification of the signal after hybridization can be achieved by removing the inactivating compounds from the 5' end of the second component 404 structure which has already bound to the first component 403. One method for achieving this is based on the inventors' previous work, described in U.S. Pat. 6,410,327. In this approach, a cage compound is attached to the 5' end to inactivate loop structure formation and prevent hybridization to the 3' regions of other 404 structures in solution. After hybridization with 403, the filament is moved into a chamber which does not contain any 404 except that bound to 403. In this chamber, a 355 nm light source is used to remove the cage groups from the 5' end of the 404 structures bound to structure 403. The filament is then returned to the chamber containing additional liquid phase 404 structures. Additional copies of 404 structures then hybridize through 3' regions with the filament-borne 404 structures with activated 5' regions. This process can be repeated as many times as necessary to achieve a detectable signal.

Still referring to FIG. 4, repeated round of hybridization amplification 406 can provide subsequent wash steps followed by activation and reapplication of inactivated second component 403 and can preferentially build up the fluorescence signal in regions where target DNA has bound to the filament 100. This multi-step process can be achieved quite readily by moving the filament between a wash station, and activation station, a hybridization station and a detection station. Once a discrimination among possibilities has been achieved, the device moves on to the next test section of the filament. The second component 404 can be designed to be the same for each amplification reaction. It may be either linear of a branched structure. The branched structure can achieve more rapid amplification. This may increase the likelihood of generating useable data from microarray analysis in a manner analogous to real time PCR.

3. Automation

In many of the preceding embodiments, there are numerous advantages in automating the procedures. Any or all of the processing, hybridization, and scanning steps may be automated, while a filament is pulled through a series of chambers and detectors. One skilled in the art will appreciate the several advantages or automation which include lower costs, increased speed and less reliance of technicians to achieve reliable and repeatable data. Levels of hybridization can also measured directly, obviating the need from cumbersome conversion to images followed by image analysis to interpret data.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The inventors have identified several key components that are critical to the success of this new platform technology. These are the identification of an appropriate fiber, development of the small volume reaction compartment with immiscible surface tension valves, and a specialized apparatus for computer controlled fiber transport through multiple reaction chambers to demonstrate automation capabilities. As outlined in the results below, preliminary evidence shows the role that each of these key components plays.

The inventors examined a number of commercial filaments with small diameters as probe carrier candidates. These were evaluated and scored with respect to diameter, inherent fluorescence, flexibility, and solubility in compounds being considered for valves. Nylon filaments were assessed for their solubility in formic acid as a method to increase surface area.

The inventors gathered a number of small diameter fibers from commercial sources. The main criteria were that the fiber had to have a small diameter, relatively low intrinsic fluorescence and the potential for coupling DNA probes to the fiber surface. Table 1 shows the results of our preliminary evaluation of a number of commercially available filaments.

TABLE 1

Fibers Evaluated to Date

| Name | Composition | Diameter (mm) | Fluorescence | | | | Flexibility | Solubility | |
| | | | Cy-3 | Cy-5 | Rh | Fluoro | | Valve Compounds | Formic Acid |
|---|---|---|---|---|---|---|---|---|---|
| Spiderline | monofilament | 0.27 | N | N | N | N | Y | N | N/A |
| Optic Fiber Glass | glass | 0.4 | N | N | N | N | N | N | N/A |
| Stren | Fluorocarbon | 0.4064 | N | N | N | Y | Y | N | N/A |
| ANDE #12 | monofilament | 0.3048 | Y | N | N | N | Y | N | N/A |
| ANDE #6 | monofilament | 0.1778 | Y | N | N | N | Y | N | N/A |
| Dupont .014 | Nylon | 0.3556 | N | N | N | N | Y | N | N |
| Dupont .012 | Nylon | 0.3048 | N | N | N | N | Y | N | N |
| Silk Thread | silk | 0.1683 | N | N | N | Y | Y | N | N/A |
| Wonder Invisible | Nylon | 0.0897 | N | N | N | N | Y | N | N/A |
| Sulky Invisible | Nylon | 0.1165 | N | N | N | N | Y | N | N/A |

Figure 5:
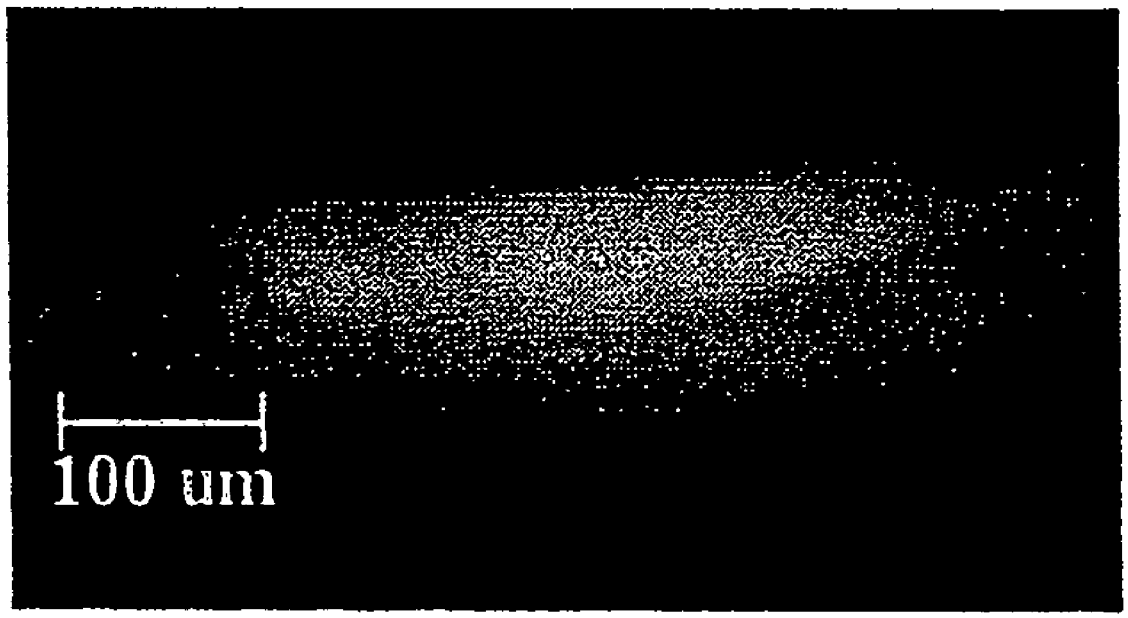
FIG. 5 shows microscopy of fluorescence from Cy-3 probe DNA attached to Sulky Invisible filament after processing.

Each of these candidate filaments was evaluated for coupling probe DNA by depositing Cy-3 labeled probe DNA onto the filament manually by pipette (see detailed methods). The printed filaments were UV cross linked by exposing them UV light and processed to remove unattached DNA (see detailed methods). Processed filaments were imaged under a Cy-3 fluorescence microscope. FIG. 5 shows the fluorescence from attached probe DNA on the Sulky Invisible filament (www.webofthread.com). This filament demonstrated the highest levels of DNA attachment so it was selected for use in the hybridization studies.

Figure 6:
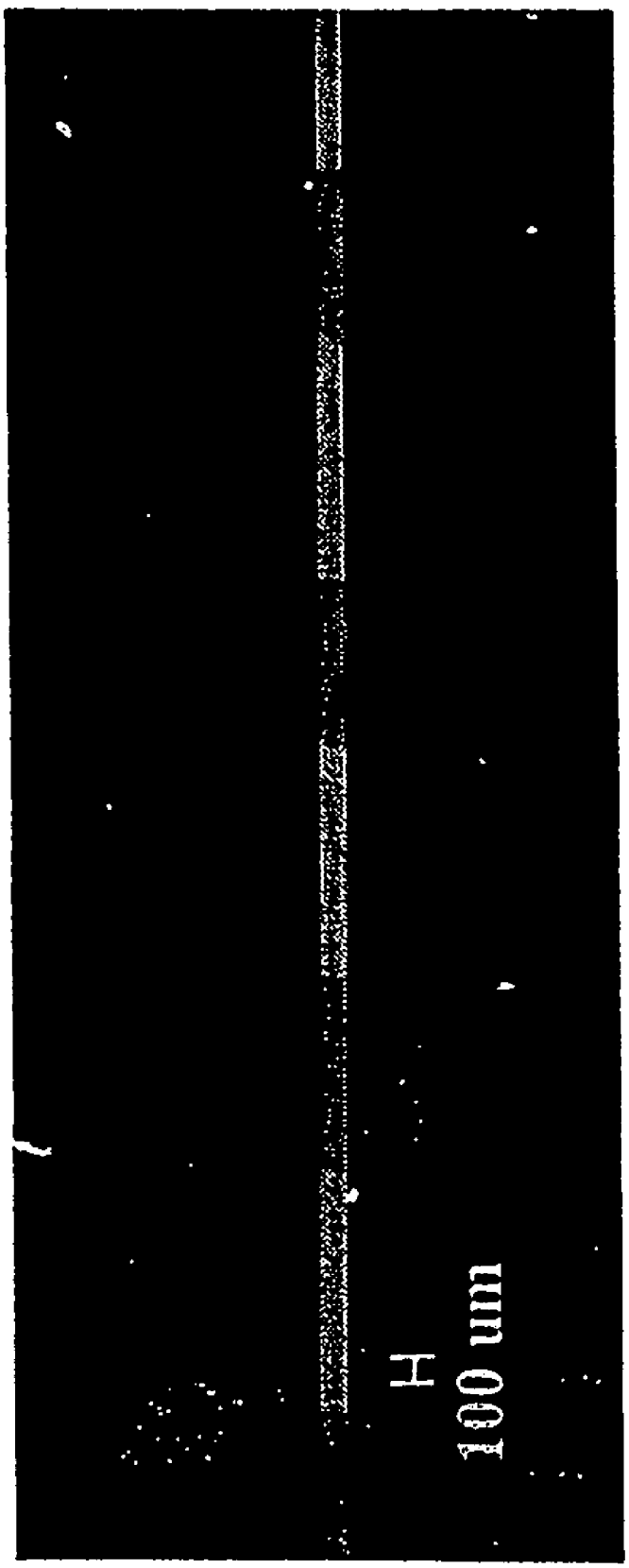
FIG. 6 shows Cy-3 and Cy-5 fluorescence image of Sulky Invisible filament hybridized by differentially labeled target molecules in static hybridization tube

To test filament hybridization, alternating segments of two different samples of unlabeled probe DNA were deposited by pipette onto a length of Sulky Invisible filament (see detailed methods). After printing, the probes were cross-linked to the filament as described previously and pre-hybridized for 30 minutes in blocking solution (see detailed methods). The filament was threaded through a 25 µl tube that had been pre-treated in the blocking solution and the tube was filled with hybridization solution containing differentially labeled target DNA homologous for the probes on the filament (see detailed methods). The filament and hybridization tube were placed in a conventional microarray hybridization compartment and immersed in a 42° C. water bath for 12 hours. After hybridization, the filament was processed (see detailed methods), taped to a microscope slide to facilitate handling, and imaged with an Axon 4000B microarray scanner. FIG. 6 shows the image of the hybridized filament indicating regions of Cy-3 (green) and Cy-5 (red) target hybridization. Fluorescence levels were approximately 6 and 10 times greater than background for the Cy-3 and Cy-5 hybridized regions respectively. These series of tests clearly illustrate that fundamental principals of DNA microarray technology like probe attachment and hybridization can be applied to filament based hybridization methods. Sufficient levels of probe attachment and hybridization can be achieved even when using a nylon substrate widely considered to be unsuitable for fluorescence microarray analysis due to high background levels.

Figure 7:
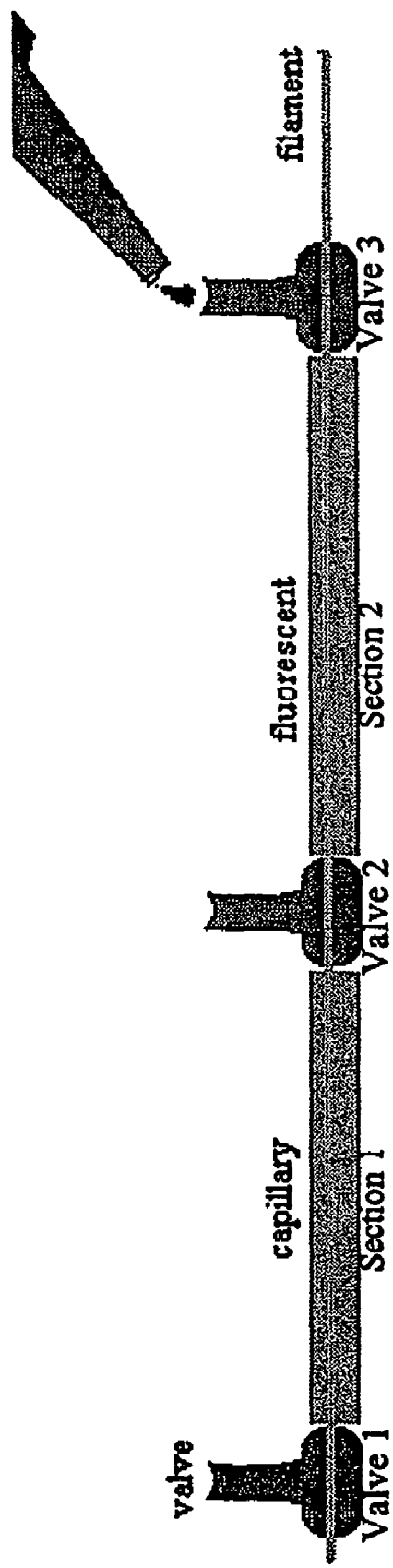
FIG. 7 is a schematic of the prototype micro vessel reaction compartment used to test valve compounds. Filament moved cyclically left to right. This set-up was used to evaluate the carryover of sodium fluorescein between contiguous compartments separated by a liquid valve.

The Handbook of Organic Solvents was referenced to establish a group of chemicals possessing desired qualities of a low vapor pressure and surface tension. Seven compounds for further testing were selected: dodecane, 1-dodecene, tridecane, methyl oleate, acetophenone, propyl benzoate, 1-methylnaphthalene. Each of these had a vapor pressure significantly less than 1 kPa and a surface tension between 25 to 40 nN/m (Handbook of Organic Solvents, Lide (1995). These chemicals were tested for their ability to act as a valve between a solution of 3×SSC with sodium fluorescein and 3×SSC without fluorescence (FIG. 7). The valve solution occupied the valve located between the two solutions. Its efficacy was determined by the amount of fluorescence exchange between the fluids, using the change in fluorescence of the solitary 3×SSC solution as the dependent variable. The effects of these selected chemicals were tested on various filaments, verifying that the morphology of the filaments remained unchanged. In addition, selected compounds were tested to insure that they possessed no inherent fluorescence which might interfere with the measurements.

The tubing assembly was constructed using a length of 25 µl precision volume micro capillary tubing with a 700 µm inner diameter (Drummond Scientific, Broomall Pa.). The tubing was fastened to modified fittings using epoxy. The apparatus was then secured to a slide also using epoxy. A 400 micron diameter optical glass fiber was used as the filament. The plastic cladding of the optic fiber was removed before use and then threaded through the tubing assembly. Fluorescent and non-fluorescent 3×SSC, and valve liquid were loaded into their respective compartments as depicted in FIG. 7.

The glass filament was then photographed with fluorescence microscopy using an Optronics image capturing system to establish baseline fluorescence. One end of the glass filament was attached to a programmable WPI Ultra Micro-Pump II. This device was programmed to "inject and withdraw" the stiff glass filament using virtual interfaces created in LabView resulting in a forward and backward motion of the glass filament through the three valves and two chambers of the micro vessel. The speed of the filament during these trials was 0.12 cm/sec, with the total distance of a forward or backward motion being 4.5 cm. Each trial consisted of 40 cycles of the filament traveling forward and backward through the micro vessel. At the end of the trial, a photograph was taken of each section of the micro vessel to assess fluorescence.

Figure 8:
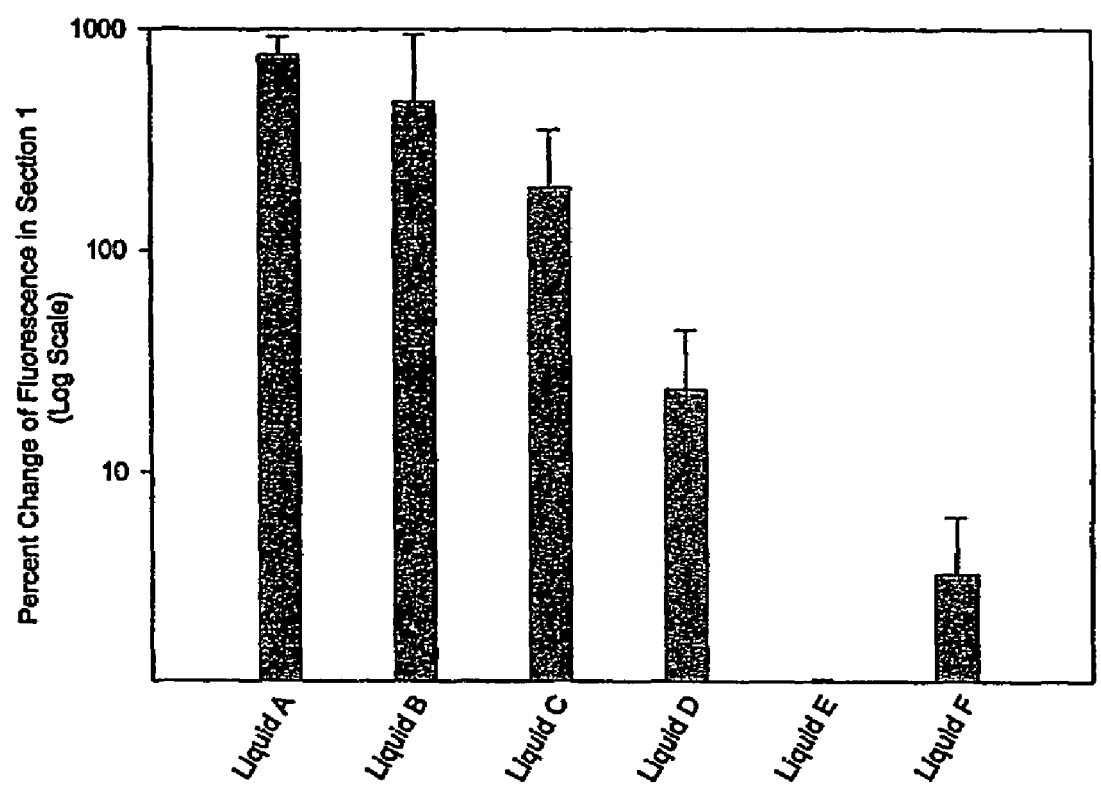
FIG. 8 shows percent change observed in the fluorescence for each of the six immiscible liquid valve candidates after 40 cycles of fiber motion.

ImagePro™ image analysis software was used to obtain a line profile and average fluorescence of each chamber. The percent change of the fluorescence was calculated using these measurements. The results of these calculations can be found in FIG. 8. Compound E (propyl benzoate) appeared to have the least carryover across the valve. Similar results were found for this valve material when it was subsequently tested using the Sulky Invisible filament transported through reaction chambers by an oscillating rotational stage.

The effectiveness of the valves at preventing evaporation of the aqueous components of the reaction compartments was assessed by weighing the complete valve system immediately after loading, and again after 24 hours at ambient room conditions. Total evaporative loss from the loaded valve assembly was less than 0.0001 g (the limit of sensitivity of the balance). Evaporative loss for the same system absent the liquid valves was in excess of 20 mg (approximately the entire aqueous volume) for the same 24-hour period.

These studies conclusively demonstrate that immiscible liquid valves can effectively seal small volume compartments for long periods of time and still permit high cycles of filament movement. By selecting the appropriate liquid valve compound, carryover between contiguous reaction compartments can be reduced to nearly undetectable levels. They also demonstrate feasibility of constructing low volume tubing compartments with liquid valve seals and the loading of the filament.

An automated filament based hybridization platform was constructed to demonstrate automated filament hybridization incorporating critical features of the design. The platform featured a 15 µl hybridization compartment sealed at each end with liquid valves. The correct hybridization temperature was maintained by means of a small heating block placed below the compartment. Filament motion was controlled within ±2 µm by a precision rotational stage. Two unique sequences of probe DNA were printed in an alternating pattern onto a length of Sulky Invisible filament, cross linked, and pre-hybridized with blocking solution. The probe filament was loaded into the hybridization compartment and attached to the rotational drive. Steady tension was maintained by a small weight attached to the end of the filament. The probe bearing segment of the filament was initially positioned outside the hybridization compartment. Hybridization solution was prepared at an identical concentration used for the static hybridization detailed previously and loaded into the tube compartment. Then the liquid valve assemblies were filled with propyl benzoate. The hybridization compartment was maintained at 42° C. by means of a small heat block place immediately below it. The rotational stage was programmed to bring the probe bearing section of the filament into the hybridization compartment at a rate of approximately one mm/sec. Once positioned, the stage moved the filament back and forth over a distance of 10,000 µm at a rate of approximately 16 µ/sec for 72 cycles. Each cycle required approximately 10 minutes and the entire 72 cycle hybridization reaction required approximately 12 hours to complete. After 72 cycles, the rotational stage moved the hybridized sections of the filament out the other end of the hybridization tube through the second liquid valve at a rate of approximately 1 mm/sec. After stopping, the filament was removed from the device and post processed and scanned in the manner described previously.

Figure 9:
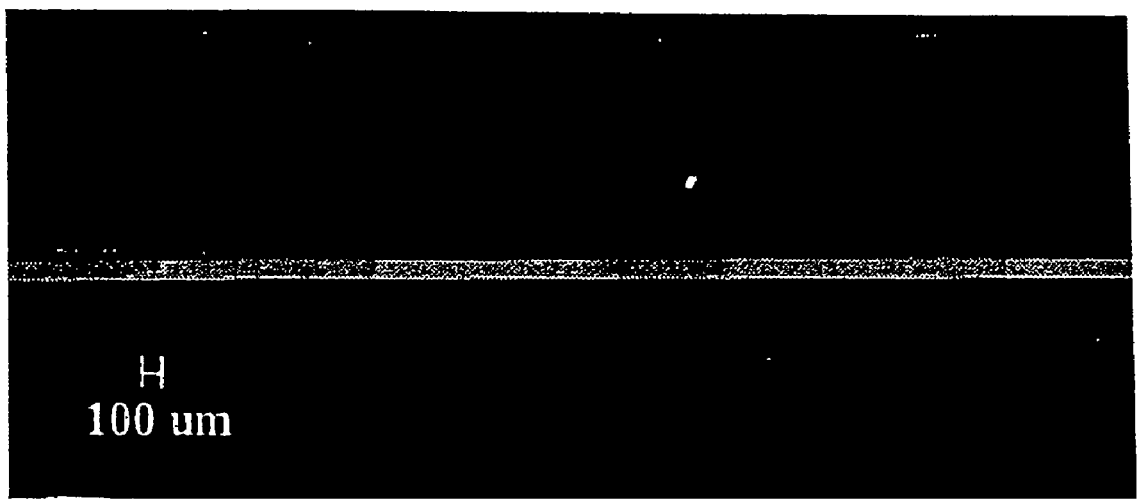
FIG. 9 shows Cy-3 and Cy-5 fluorescence image of Sulky Invisible filament hybridized by differentially labeled target molecules in a computer actuated dynamic hybridization experiment.

FIG. 9 shows the Cy-3 and Cy-5 fluorescence from the hybridized filament. Fluorescence levels were comparable to the filament hybridized under static conditions. A control filament hybridized with another aliquot of the same hybridization solution and hybridized under static conditions produced similar results. These tests conclusively demonstrate the feasibility of several critical components of an automated filament based hybridization system. Hybridization of probe bearing filament was conducted in a small volume compartment sealed by liquid valves. The contents of the compartment were temperature controlled and were contained and protected from evaporation during continuous filament movement over a period of 12 hrs. Programmable high-precision filament movement was achieved by a computer controlled rotational stage. Exposure of filament bound probes to the liquid valves before and following hybridization had no noticeable effect on hybridization compared to an identical filament hybridized under static conditions with identical hybridization solution.

Example 2

An capture antibody attached to a filament was used to bind virus in solution. Virus captured by the filament bound antibody was then quantified by a second antibody reaction with a fluorescently labeled antibody. With the exception of the initial deposition of the capture antibody, all chemical reaction steps were carried out under automated computer control to move the filament through the interior of 5 liquid filled capillary tubes containing reagents required in the reaction.

A probe or "capture" antibody attached to a filament was made as follows: unlabeled anti-m13 antibody was spotted onto a Sulky Invisible polyester filament (~130 µm diameter) at a concentration of 200 µl/ml and was left to incubate at room temperature in a damp box for approximately 40 min. Following incubation, the spots were briefly rinsed in phosphate buffered saline with 0.1% tween 20 (PBS-T).

Five 25 µl chambers were constructed using microcapillary tubes. The capillary tubes were 65 mm long with an outer diameter of 970 µm and an inner diameter of 701 µm.

The fiber was mounted on a rotational stage, passed through each of the capillary tubes and configured into a closed loop under tension The spots on the string were then moved into the blocking chamber containing PBS-T and slowly oscillated for approximately 35 min. When this blocking step was completed the spots were moved to the second chamber containing m13 virus ($3.3 \times 10^{11}$ virions/ml) and oscillated for 30 minutes, after which the spots were rinsed for approximately 5 minutes in chamber 3 containing PBS-T. Next, the spots were positioned in chamber 4 with Alexa Fluor 555 labeled anti-m13 antibody (~340 µg/ml) and left to oscillate for 35 min. The final step involved positioning the spots in the fifth chamber containing PBS-T and oscillating the spots for 5 min as a final rinse.

Following the final rinse step, the string was removed from the chambers and taped to a glass microscope slide. The slide was inserted into a Genepix 4000 microarray scanner. The focus position was adjusted to 150 µm to account for the raised height of the filament on the glass slide. The slide was then scanned at different power levels until an optimal signal intensity was obtained.

Figure 11:
FIG. 11 shows an example of antibody capture of virus in solution. Capture antibody was found to a filament, and captured virus was quantified by a second antibody with a fluorescent label (1—no antibody; 2-4 with antibody).

FIG. 11 shows the fluorescence signal from 4 regions of the fiber after scanning. The left-most region contains no capture antibody and the three on the right contain triplicate capture antibody as described above.

All the disclosed embodiments of the invention disclosed herein can be made and used without undue experimentation in light of the disclosure. The invention is not limited by theoretical statements recited herein. Although the best mode of carrying out the invention contemplated by the inventors is disclosed, practice of the invention is not limited thereto. Accordingly, it will be appreciated by those skilled in the art that the invention may be practiced otherwise than as specifically described herein.

Further, the individual components need not be formed in the disclosed shapes, or combined in the disclosed configurations, but could be provided in virtually any shapes, and/or combined in virtually any configuration. Further, the individual components need not be fabricated from the disclosed materials, but could be fabricated from virtually any suitable materials.

Further, variation may be made in the steps or in the sequence of steps composing methods described herein. It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

F. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 5,214,136
U.S. Pat. No. 5,223,618
U.S. Pat. No. 5,378,825
U.S. Pat. No. 5,446,137
U.S. Pat. No. 5,466,786
U.S. Pat. No. 5,470,967
U.S. Pat. No. 5,602,240
U.S. Pat. No. 5,610,289
U.S. Pat. No. 5,614,617
U.S. Pat. No. 5,623,070
U.S. Pat. No. 5,652,099
U.S. Pat. No. 5,670,663
U.S. Pat. No. 5,672,697
U.S. Pat. No. 5,700,922
U.S. Pat. No. 5,708,154
U.S. Pat. No. 5,714,606
U.S. Pat. No. 5,763,167
U.S. Pat. No. 5,777,092
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 6,410,327
Handbook of Organic Solvents, Lida (Ed.), 1995.
Kornberg and Baker, DNA Replication, 2nd Ed., Freeman, San Francisco, 1992.
Scheit, "Nucleotide Analogs," In: Synthesis and Biological Function, Wiley-Interscience, New York, pp. 171-172, 1980.
Holle et al., *Electrophoresis* 1:157-264, 2000.

The invention claimed is:

1. A method of detecting target-probe interactions comprising:
    (a) providing a filament with a plurality of a first probe disposed in an annular fashion thereon;
    (b) traversing the filament through a first chamber, wherein the first chamber contains the target in solution; and
    (c) assessing binding of the target to a member of the plurality of the first probe.

2. The method of claim 1, wherein the plurality of the first probe is associated with a probe identifier.

3. The method of claim 2, wherein the probe identifier is a bar code.

4. The method of claim 3, wherein the bar code is disposed in an annular fashion.

5. The method of claim 3, wherein the bar code is disposed in a linear fashion.

6. The method of claim 1, wherein the filament has a plurality of different probes disposed thereon.

7. The method of claim 6, wherein the plurality of different probes are disposed in a single ring around the filament.

8. The method of claim 7, wherein each of the plurality of different probes is associated with a distinct probe identifier.

9. The method of claim 1, further comprising traversing the filament through a second chamber, wherein the second chamber contains a solution that lacks the target.

10. The method of claim 9, wherein the second chamber comprises a solution for pre-processing or post-processing of the filament.

11. The method of claim 10, wherein the preprocessing comprises making an array, chemical blocking of a reactive group on the target, ionic blocking of a target, or denaturing of a target.

12. The method of claim 10, wherein the post-processing comprises deblocking of a reactive group on the target, removal of an ionic blocker, or renaturing of a target molecule.

13. The method of claim 1, wherein the target is labeled with a fluorescent label, a chemilluminescent label, a radioactive label, a magnetic label, or a spin resonance label.

14. The method of claim 1, further comprising convective transport of the target solution by means of filament movement through the first chamber.

15. The method of claim 14, further comprising re-circulating target solution from the first chamber.

16. The method of claim 1, wherein the filament comprises surface features to enhance mixing of the target solution.

17. The method of claim 1, wherein the first chamber comprises surface features to enhance mixing of the target solution.

18. The method of claim 1, wherein the filament is transparent.

19. The method of claim 1, wherein the filament is adapted to incorporate an electrical charge.

20. The method of claim 19, further comprising subjecting the target to electrophoretic movement.

21. The method of claim 20, wherein the electrophoretic movement promotes target-probe interaction.

22. The method of claim 20, wherein the electrophoretic movement inhibits target-probe interaction.

23. The method of claim 1, further comprising a second traversing of the filament through a chamber comprising the target.

24. The method of claim 23, wherein the chamber used for the second traversing is the same chamber in step (b).

25. The method of claim 23, wherein the chamber used for the second traversing is a different chamber than in step (b).

26. The method of claim 23, wherein a temperature in the chamber used for the second traversing is altered from that used in step (b).

27. The method of claim 23, wherein a charge in the chamber used for the second traversing is altered from that used in step (b).

28. The method of claim 23, wherein a current, amperage, voltage or polarity in the chamber used for the second traversing is altered from that used in step (b).

29. The method of claim 1, further comprising enhancing detection of binding of the target to the first probe.

30. The method of claim 29, wherein enhancing comprises traversing the filament through a second processing chamber that contains
   (i) a second liquid phase probe that binds to the target at a location distinct from the first probe, and wherein the second liquid phase probe contains a binding site for a third liquid phase probe; and
   (ii) a third liquid phase probe that is detectable.

31. The method of claim 30, wherein the third liquid phase probe is provided in an inactive state and then activated to facilitate amplification.

32. The method of claim 31, wherein the third liquid phase probe is labeled with a fluorescent, a chemiluminescent or a radioactive molecule.

33. The method of claim 31, wherein the third liquid phase probe is a linear molecule with a binding site for itself.

34. The method of claim 31, wherein the third liquid phase probe is a branched molecule with multiple binding sites for itself.

35. The method of claim 1, wherein the filament is 1 μm to about 0.5 cm in diameter.

36. The method of claim 1, wherein the processing chamber is greater than 1 μm in diameter and less than 2.0 cm.

37. The method of claim 1, wherein the target solution in the processing chamber is present in a volume of less than 100 μl.

38. The method of claim 1, wherein the filament comprises an axial or radial probe density of greater than 1 probe region per cm.

39. A method of detecting target-probe interactions comprising:
   (a) providing a filament with a plurality of different probes disposed thereon;
   (b) traversing the filament through a first chamber, wherein the first chamber contains the target in solution; and
   (c) assessing binding of the target to more than one of the probes.

40. The method of claim 39, wherein the plurality of probes are disposed on said filament in annular fashion.

41. The method of claim 39, wherein the plurality of probes is associated with a probe identifier.

42. The method of claim 41, wherein the probe identifier is a bar code.

43. The method of claim 42, wherein the bar code is disposed in a linear fashion.

44. The method of claim 39, wherein each of the plurality of different probes is associated with a distinct probe identifier.

45. The method of claim 39, further comprising traversing the filament through a second chamber, wherein the second chamber contains a solution that lacks the target.

46. The method of claim 45, wherein the second chamber comprises a solution for pre-processing or post-processing of the filament.

47. The method of claim 46, wherein the preprocessing comprises making an array, chemical blocking of a reactive group on the target, ionic blocking of a target, or denaturing of a target.

48. The method of claim 46, wherein the post-processing comprises deblocking of a reactive group on the target, removal of an ionic blocker, or renaturing of a target molecule.

49. The method of claim 39, wherein the target is labeled with a fluorescent label, a chemilluminescent label, a radioactive label, a magnetic label, or a spin resonance label.

50. The method of claim 39, wherein the bar code is disposed in an annular fashion.

51. The method of claim 39, further comprising convective transport of the target solution by means of filament movement through the first chamber.

52. The method of claim 51, further comprising re-circulating target solution from the first chamber.

53. The method of claim 39, wherein the filament comprises surface features to enhance mixing of the target solution.

54. The method of claim 39, wherein the first chamber comprises surface features to enhance mixing of the target solution.

55. The method of claim 39, wherein the filament is transparent.

56. The method of claim 39, wherein the filament is adapted to incorporate an electrical charge.

57. The method of claim 39, further comprising subjecting the target to electrophoretic movement.

58. The method of claim 57, wherein the electrophoretic movement promotes target-probe interaction.

59. The method of claim 57, wherein the electrophoretic movement inhibits target-probe interaction.

60. The method of claim 39, further comprising a second traversing of the filament through a chamber comprising the target.

61. The method of claim 60, wherein the chamber used for the second traversing is the same chamber in step (b).

62. The method of claim 60, wherein the chamber used for the second traversing is a different chamber than in step (b).

63. The method of claim 60, wherein a temperature in the chamber used for the second traversing is altered from that used in step (b).

64. The method of claim 60, wherein a charge in the chamber used for the second traversing is altered from that used in step (b).

65. The method of claim 60, wherein a current, amperage, voltage or polarity in the chamber used for the second traversing is altered from that used in step (b).

66. The method of claim 39, further comprising enhancing detection of binding of the target to one of the probes.

67. The method of claim 66, wherein enhancing comprises traversing the filament through a second processing chamber that contains
   (i) a second liquid phase probe that binds to the target at a location distinct from the first probe, and wherein the second liquid phase probe contains a binding site for a third liquid phase probe; and
   (ii) a third liquid phase probe that is detectable.

68. The method of claim 67, wherein the third liquid phase probe is provided in an inactive state and then activated to facilitate amplification.

69. The method of claim 68, wherein the third liquid phase probe is labeled with a fluorescent, a chemilluminescent or a radioactive molecule.

70. The method of claim 68, wherein the third liquid phase probe is a linear molecule with a binding site for itself.

71. The method of claim 68, wherein the third liquid phase probe is a branched molecule with multiple binding sites for itself.

72. The method of claim 39, wherein the filament is 1 μm to about 0.5 cm in diameter.

73. The method of claim 39, wherein the processing chamber is greater than 1 μm in diameter and less than 2.0 cm.

74. The method of claim 39, wherein the target solution in the processing chamber is present in a volume of less than 100 μl.

75. The method of claim 39, wherein the filament comprises an axial or radial probe density of greater than 1 probe region per cm.

\* \* \* \* \*